(12) United States Patent
Peltola et al.

(10) Patent No.: US 6,632,412 B2
(45) Date of Patent: Oct. 14, 2003

(54) BIOACTIVE SOL-GEL DERIVED SILICA FIBERS AND METHODS FOR THEIR PREPARATION

(76) Inventors: Timo Peltola, Jaakkimankatu 5 D 33, FIN-20740, Turku (FI); Mika Jokinen, Mielikinkatu 5, FIN-20540, Turku (FI); Sinikka Veittola, Elementinpolku 17 B 24, FIN-33720, Tampere (FI); Antti Yli-Urpo, Värttinäkatu 17, FIN-20660, Littoinen (FI)

( * ) Notice: Subject to any disclaimer, the term of this patent is extended or adjusted under 35 U.S.C. 154(b) by 8 days.

(21) Appl. No.: 09/452,379

(22) Filed: Dec. 1, 1999

(65) Prior Publication Data

US 2002/0064493 A1 May 30, 2002

(51) Int. Cl.$^7$ .............................................. C01B 33/12
(52) U.S. Cl. ...................................................... 423/338
(58) Field of Search ...................... 423/338; 501/95.1; 428/364; 65/395, 33.3

(56) References Cited

U.S. PATENT DOCUMENTS

| | | | | |
|---|---|---|---|---|
| 4,683,128 A | * | 7/1987 | Orii et al. | 423/338 |
| 5,629,186 A | * | 5/1997 | Yasukawa et al. | 435/177 |
| 5,834,007 A | * | 11/1998 | Kubota | 424/443 |
| 6,228,437 B1 | * | 5/2001 | Schmidt | 427/559 |

FOREIGN PATENT DOCUMENTS

| | | |
|---|---|---|
| DE | 196 09 551 | 7/1997 |
| WO | WO 97/045367 | 12/1997 |

OTHER PUBLICATIONS

Hasegawa I, Nakamura T, Kajiwara M, Motojima S., "Synthesis of silicon carbide fibers by sol–gel processing," 8 *J Sol–Gel Sci Tech* 577–579 (1997).
Li et al., "Apatite Formation Induced by Silica Gel in a Simulated Body Fluid," 75 *J. Am Ceramic Soc.* 2094–97 (1992).
Hashimoto T, Kamiya K, Nasu H., "Strengthening of sol–gel–derived SiO$_2$ glass fibers by incorporating colloidal silica particles," 143 *J. Non–Cryst Sol* 31–39 (1992).
Pozo de Fernandez ME, Kang C, Mangonon PL., "Process ceramic fibers by sol–gel," 9 *Chem Eng Prog* 49–53 (1993).
Sakka S, Kamiya K., "The sol–gel transition in the hydrolysis of metal alkoxides in relation to the formation of glass fibers and films," 48 *J Non–Cryst Sol* 31–43 (1982).
Sakka S, Kozuka H., "Rheology of sols and fiber drawing," 100 *J Non–Cryst Sol* 142–153 (1988).
Shin D–Y , Han S–M., "Spinnability and rheological properties of sols derived from Si(OC$_2$H$_5$)$_4$ and Zr(O–nC$_3$H$_7$)$_4$ solutions," 1 *J Sol–Gel Sci Tech* 267–273 (1994).
Sowman HG, "A new era in ceramic fibers via sol–gel technology," 67 *Cer Bull* 1911–1916 (1988).
Sacks MD, Sheu R–S., "Rheological properties of silica sol–gel materials," 92 *J Non–Cryst Sol* 383–396 (1987).

Hasegawa I, Nakamura T, Motojima S, Kajiwara M., "Synthesis of silicon carbide fibers by sol–gel processing," 8 *J Sol–Gel Sci Tech* (1977).
Brinker CJ, Scherer GW., *Sol–Gel Science: The Physics and Chemistry of Sol–Gel Processing* 204–209 (Academic Press Inc. San Diego. CA. USA; 1990).
Kamiya K, Tanimoto K, Toshinobu T,. "Preparation of TiO2 fibers by hydrolysis and polycondensation of Ti(O–i–C$_3$H$_7$)$_4$," 5 *J Mat Sci Lett* 402–404 (1986).
Glaubitt W, Watzka W, Scholz H, Sporn D., "Sol–gel processing of functional and structural ceramic oxide fibers," 8 *J Sol–Gel Sci Tech* 29–33 (1997).
Muralidharan BG, Agrawal DC, "Sol–gel derived TiO$_2$–SiO$_2$ fibers," 9 *J Sol–Gel Sci Tech* –93 (1997).
Toyoda M, Hamaji Y, Tomono K., "Fabrication of PbTiO$_3$ ceramic fibers by sol–gel processing," 9 *J Sol–Gel Sci Tech* 71–84 (1997).
Sakka S., "Sol–gel processing of insulating, electroconducting and superconducting fibers," 121 *J Non–Cryst Sol* 417–423 (1990).
Del Olmo L, Caldaza ML., "PbTiO3 ceramic fibers prepared from a sol–gel process as piezoelectic materials," 121 *J Non–Cryst Sol* 424–427 91990).
Yoko T, Kamiya K, Kanaka K., "Preparation of multiple oxide BaTiO$_3$ fibers by the sol–gel method," 25 *J Mat Sci* 3922–3929 (1990).
Katayama S, Sekine M., "Fabrication of superconducting YBa$_2$Cu$_3$O$_7$–x fibers by the sol–gel method using metal alkoxides," 6 *J Mater Res* 1629–1633 (1991).
Venkatasusubramanian N, Wade B, Desai P, Abhiraman., "Synthesis and characterization of spinnable sol–gel derived polyborates," 130 *J Non–Cryst Sol* 144–156 (1991).
Selvaraj U, Prasadarao A V, Komameni S, Brooks K, Kurtz S., "Sol–Gel processing of PbTiO$_3$ and Pb(Zr$_{0.52}$Ti$_{0.48}$)O$_3$ fibers," 7 *J Mat Res* 992–996 (1992).
Yoso T, Iwahara H., "Synthesis of β–alumina fiber from modified aluminum alkoxide precursor," 27 *J Mat Sci* 1499–1504 (1992).
Seddon AB., "Applicability of sol–gel processing in production of silica based optical fibers," 9 *Mat Sci Tech* 729–736 (1993).
Emig G, Fitzer E, Zimmerman–Chopin R., "Sol–gel process for spinning of continuous (Zr,Ce)O$_2$ fibers," A189 *Mat Sci Eng* 311–317 (1994).

(List continued on next page.)

*Primary Examiner*—Stanley S. Silverman
*Assistant Examiner*—Edward M. Johnson
(74) *Attorney, Agent, or Firm*—James C. Lydon

(57) ABSTRACT

This invention relates to bioactive sol-gel derived silica fibers, methods for their preparation, an implantable device comprising the fibers and the use of the device for tissue guiding or bone repair.

21 Claims, 13 Drawing Sheets

OTHER PUBLICATIONS

Emig G. Wirth R, Zimmermann–Chopin R., "Sol1gel–based precursors for manufacturing refractory oxide fibers," 29 *J Mat Sci Lett* 4559–4566 (1994).

Chiou YH, Tsai MT, Shih HC., "The preparation of alumina fiber by sol–gel processing," 29 *J Mat Sci* 2378–2388 (1994).

Narang U, Gvishi R, Bright FV, Prasad PN., "Sol–gel–derived micron scale optical fibers for chemical sensing," 6 *J Sol–Gel Sci Tech* 113–119 (1996).

Matejec V, Hayer M, Pospisilova M, Kasik I., "Preparation of optical cores of silica optical fibers by the sol–gel method," 8 *J Sol–Gel Sci Tech* 889–893 (1997).

Jokinen M, Peltola T, Veittola S, Rahiala H, Rosenholm JB., "Biodegradable Ii ceramic fibres from silica sols," 20 *J Eur Ceram Soc* 1739–1748 (2000).

Hench L., "Bioactive ceramics: Theory and clinical applications," 7 *Bioceramics* 3–14 (1994).

Voigt C, Mtiller–Mai C, Kandilakis K, Kangasniemi I, Yli–Urpo A, Gross U., "Biological reaction after implantation of sol–gel activated titanium cylinders in the distal epiphysis of the rabbit femur," 13th European Conference on Biomaterials 42–45 (Goteborg, Sweden 1997), Kokubo T, Kushitani H, Sakka S, Kitsugi T, Yamamuro T., "Solutions able to reproduce in vivo surface–structure changes in bioactive glass–ceramic A–W3," 24 *J Biomed Mater Res* 721–734 (1990).

Koch OG, Koch–Dedic GA, *Handbuch der Spurenanalyse* 1105 (Berlin Springer–Verlag 1974).

Rehman I, Bonfield W., "Characterization of hydroxyapatite and carbonated apatite by photo acoustic FTIR spectroscopy," 8 *J Mater Science. Mater Medicine* 1–4 (1997).

Peltola T, Jokinen M, Rahiala H, Levanen E, Rosenholm JB, Kangasniem I, Yli–Urpo A., "Calcium phosphate formation on porous sol–gel derived $SiO_2$ and $CaO-P_2O_5-SiO_2$ substrates in vitro," 44 *J Biomed Mater Res* 12–21 (1999).

Pereira MM, Hench LL., "Mechanisms of hydroxyapatite formation on porous gel–silica substrates," 7 *J Sol–Gel Sci Tech* 59–68 (1996).

Andersson OH, Kangasniemi I,. "Calcium phosphate formation at the surface of bioactive glass in vitro," 25 *J Biomed Mater Res* 1019–1030 (1991).

Peltola T, Jokinen M, Rahiala H, patsi M, Heikkila J, Kangasniemi I, Yli–Urpo A., "Effect of aging time of sol on structure and in vitro calcium phosphate formation of sol–gel derived titania films," 51 *J Biomed Mater Res* 200–208 (2000).

Jokinen M, patsi M, Rahiala H, Peltola T, Ritala M, Rosenholm Jarl B., "Influence of sol and surface properties on in vitro bioactivity of sol–gel derived $TiO_2$ and $TiO_2-SiO_2$ films deposited by dip coating method," 42 *J Biomed Mater Res* 295–302 (1998).

* cited by examiner

BIOACTIVE SOL-GEL DERIVED SILICA FIBERS AND METHODS FOR THEIR PREPARATION

This invention concerns bioactive sol-gel derived silica fibers, methods for their preparation, an implantable device comprising said fibers and the use of said device for tissue guiding or bone repair.

BACKGROUND OF THE INVENTION

The publications and other materials used herein to illuminate the background of the invention, and in particular, cases to provide additional details respecting the practice, are incorporated by reference.

The sol-gel method has widely been used as an alternative method to prepare a great variety of applications including monoliths, powders, coatings and fibers. A growing field of interest has been bioceramics that can be used as implants, fillers, or drug delivery devices.

The rheological properties of the silica sols and the processing of the sol-gel derived silica fibers are well known.[1-9] The most common property of the sols in the fiber spinning is a low water-to-TEOS molar ratio (about 2) (TEOS=tetraethylorthosilicate or tetraethoxysilane). The low water-to-TEOS ratio indicates a formation of linear silica polymers, which is an important factor for the spinnable sols. Various sol-gel derived fibers (containing Ti, Si, A, Pb, Y, Mg or Al) have also been successfully prepared.[5,6,10-13] The most common use for these fibers are the applications for optical and electronic purposes.[14-27]

In general, the fibers have been used to improve mechanical properties in different materials. The bulk structure of the sol-gel derived silica fibers can be varied by controlling the degree of branching of silica clusters. The heat treatment of the fibers is another known method for condensing the bulk structure. The mechanical properties become better after heat-treatment at high temperatures. In applications where the fibers are used as drug delivery device in soft tissue, the mechanical properties are of minor importance. If better mechanical properties are needed, it has to be noted that the biodegradation reduces after heat-treatment at high temperatures. In the inventors' previous article[28] the biodegradation of the sol-gel derived silica fibers (which was not heat-treated) was studied. It was found that the biodegradation of the green state fibers can be varied and controlled by adjusting the stage of spinnability (by varying the spinning moment) and the viscosity of the sol. It was found that fibers spun in the early stage of spinnability degrade more slowly in the simulated body fluid (SBF) than fibers spun at a later stage.

Another important property of the biomaterials, bioactivity, has been widely studied also for sol-gel-derived materials. The ability of the materials to form HCA (HCA= bone like calcium phosphate) may lead to osteoconduction and further to bone bonding in in vivo conditions.[29,30]

The formation of the HCA layer can be simulated in an in vitro environment by using simulated body fluid. The SBF solution contains inorganic ions in concentrations corresponding to the human blood plasma.[31] The formed HCA has several characteristics similar to the apatite in the bone tissue and it is thought to be formed by an inorganic chemical reaction in vitro similar to that occurring in the bone tissue. This in vitro bioactivity test is generally accepted to give an indication of the in viva bioactivity.[32]

Bioactive sol-gel-derived silica fibers are not mentioned in prior art. Such bioactive silica fibers would provide alternatives for the design of novel products, for example implantable devices to be used in tissue guiding or bone repairs.

OBJECTS AND SUMMARY OF THE INVENTION

The aim of this invention is to provide a bioactive sol-gel derived silica fiber. The aim is particularly to provide a sol-gel derived silica fiber, the solubility and bioactivity of which can be varied within a wide range and where the solubility and bioactivity can be varied to some extent independently of each other.

Another object is to provide a method for the preparation of a bioactive sol-gel derived silica fiber of the aforementioned kind.

Still one object is to achieve an implantable device based on the aforementioned fiber, optionally loaded with a biologically active agent, wherein said device preferably is in the form of a woven or non-woven mat, a knitted fabric or a braided cord, particularly suitable for use as tissue guiding or bone repair.

Thus, according to one aspect, this invention concerns a bioactive sol-gel derived silica fiber spun from a sol at a starting point of the spinning process corresponding to a sol viscosity of at least 2000 cP, after which said fiber has been subjected to i) heat treatment or ii) aging.

According to another aspect, this invention concerns a method for the preparation of a bioactive sol-gel derived silica fiber, said method comprising spinning the fiber from a silica sol wherein the starting point of the spinning process corresponds to a sol viscosity of at least 2000 cP, followed by i) heat treating or ii) aging of the fiber.

According to a further aspect, this invention concerns an implantable device comprising a fiber according to this invention.

Furthermore, this invention concerns the use of the implantable device according to this invention for tissue guiding or bone repair.

DETAILED DESCRIPTION OF THE INVENTION

Figure 1A:
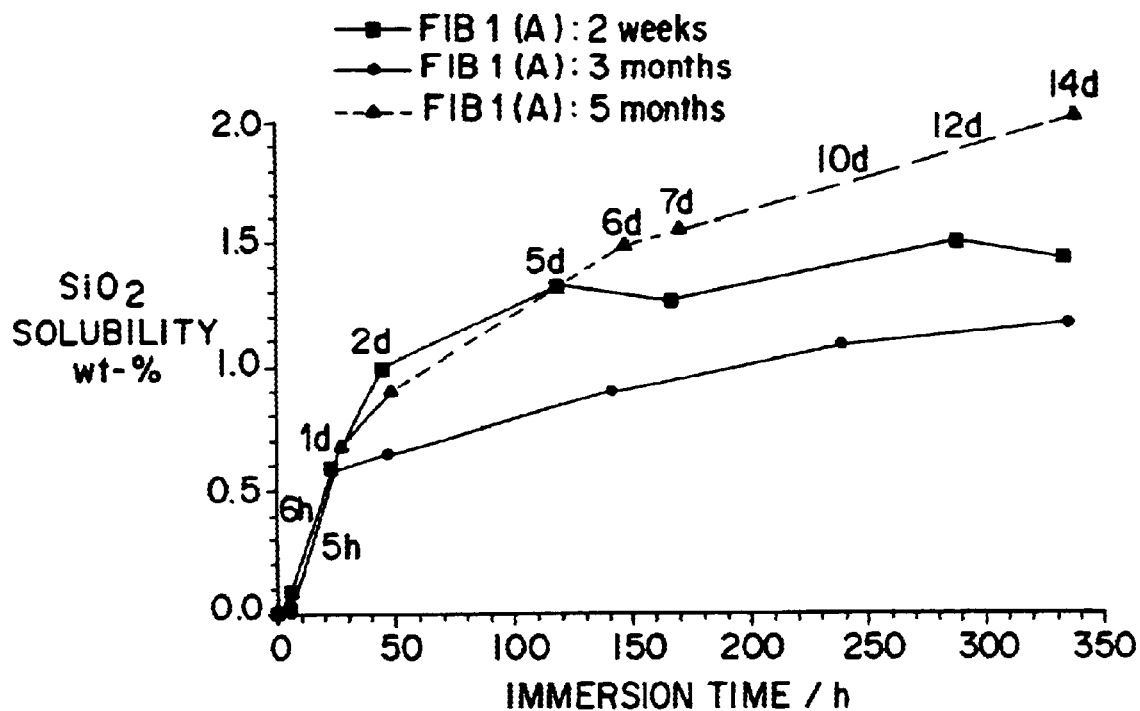
FIGS. 1a to 1f show the $SiO_2$ solubility as function of immersion time in SBF for different sol-gel derived $SiO_2$ fibers aged for 2 weeks, 3 months and 5 months, respectively.
Figure 1B:
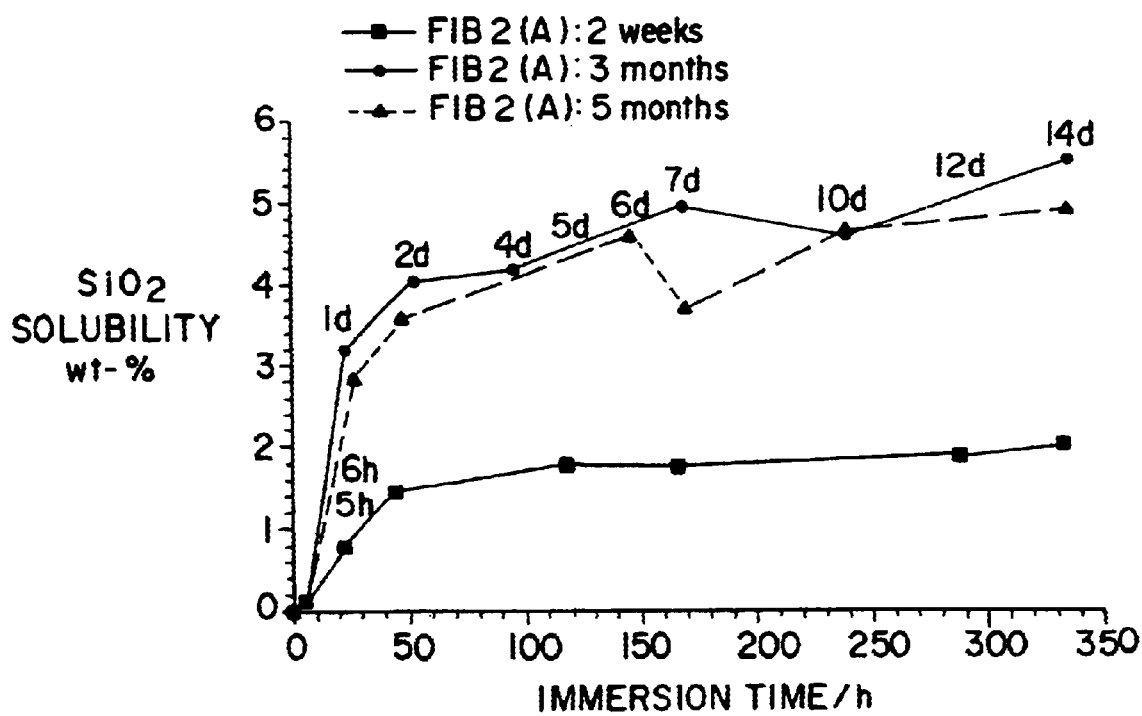
Figure 1C:
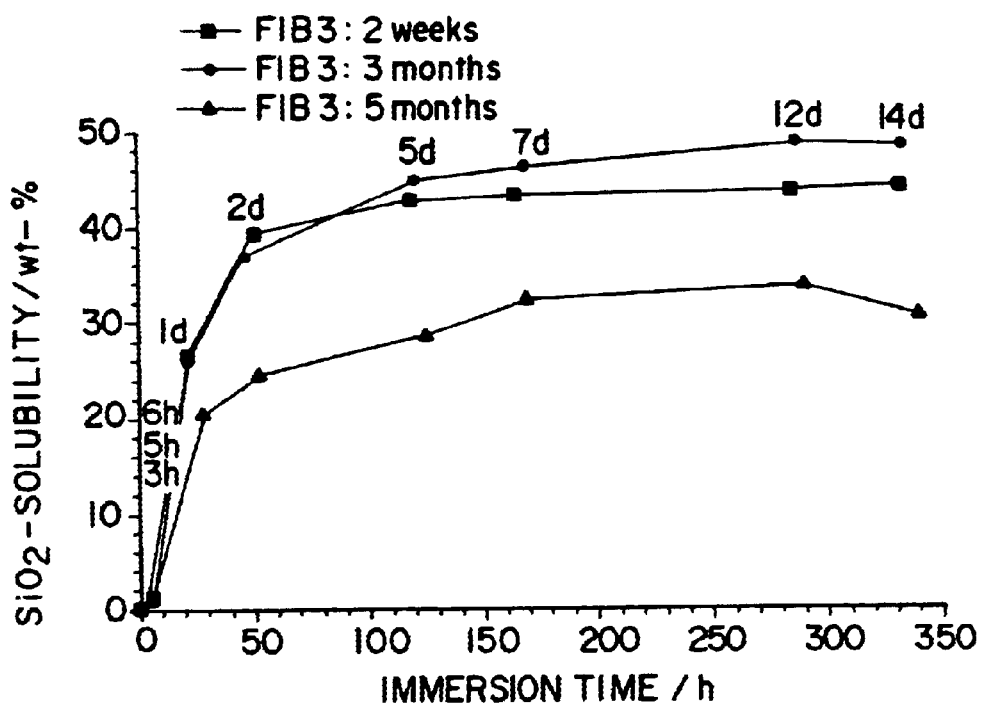

The effect of aging and heat treatment on the bioactivity of the fibers according to this invention is stronger for fibers spun from sols of higher viscosity than for fibers spun from sols at lower viscosity. Thus, in order to get a good bioactivity, the starting point for the spinning of the fibers should preferably be at a sol viscosity of at least 3000 cP.

The heat treatment should be carried out for a sufficient time, for example 2 hours, in a temperature range of 150 to 250° C., preferably 150 to 200° C., most preferably about 175° C.

If the bioactivity is created by aging of the fiber, the aging should preferably be carried out at a rather low temperature, preferably at room temperature, for a period of 2 weeks to about 5 months, preferably for about 3 to 5 months.

The effect of aging on the solubility (biodegradability) of the fibers according to this invention is stronger for fibers spun from sols of higher viscosity than for fibers spun from sols at lower viscosity. Thus, in order to get fibers having increased solubility, the starting point of the spinning of the fibers should preferably start at a sol viscosity of at least 3000 cP. If fibers with high bioactivity and rather low solubility are desired, the bioactivity of the fibers shall preferably be generated by heat treatment of the fibers. On the other hand, if slightly bioactive fibers with high solubility are desired, the fibers shall preferably be aged instead of heat treated.

If fibers of moderate bioactivity and low solubility are desired, such fibers shall preferably be created by spinning at low (<3000 cP) viscosity followed by heat treatment at about 175° C.

If a moderately bioactive fiber loaded with a biologically active agent, e.g. a therapeutically active agent is desired, said agent is preferably added to the sol before spinning. In this case the bioactivity is preferably created by aging of the fiber, or with low temperature heat treating in order to avoid adverse effects of the heat on the biologically active agent.

Preferable biologically active agents are especially agents useful to facilitate the biocompatibility of the implanted device in the mammalian body and to avoid complications after the operation. Thus, as examples of useful biologically active agents can be mentioned antiinflammatory, antimicrobial and tranquilizing agent, antithrombotic agents, growth factors and the like.

The implantable device can be made of one single kind of fibers according to this invention. Alternatively, the device can comprise a mixture of two or more kinds of fibers according to this invention. In this case a certain fiber may be loaded with a biologically active agent while the other fibers may be unloaded. Alternatively, all kinds of fibers may be loaded with a biologically active agent. The device can further comprise other components, for example fillers or fibers known per se. By choicing appropriate kinds and amounts of different fibers and optionally other components, implantable devices of desired properties, such as strength, bioresorbability, bioactivity etc. can be achieved.

According to a preferred embodiment, the device according to this invention, is in the form or a woven or non-woven mat, a knitted fabric or a braided cord.

The invention will be described more in detail in the Experimental section in the following non-limiting examples.

Experimental

The objective of the experiments was to study the effect of aging or heat treatment on the solubility (biodegradability) and the calcium phosphate formation ability (bioactivity) of the different potentially bioactive sol-gel-derived green state silica fibers. Various fibers with different bulk structures were prepared by changing the composition (varying the catalyst) and controlling the stage of spinnability and viscosity of the sol. The influence of aging time or temperature in the heat treating step of the fibers on the bulk structure of the samples was investigated. Furthermore, the ability to form calcium phosphate was investigated indirectly in terms of structural changes of the fibers by the solubility test. The in vitro bioactivity and solubility tests were cried out in a simulated body fluid. Dry spinning was used to prepare fibers.

Materials and Methods

Sol-Gel-Derived $SiO_2$ Fibers

The green state fibers were prepared using the sol-gel method and dry spinning technique. The silica sols were prepared from tetraethylortosilicate (TEOS), deionised water, absolute ethanol and $HNO_3$ or $NH_3$ as catalysts. The sol compositions in molar ratios of the different fibers prepared are shown in Table I. TEOS (500 g) was mixed with ethanol and $HNO_3$ with water. The acid/water solution was added to the TEOS/ethanol solution under vigorous sting and then the solution was poured into an evaporating dish. The evaporating dish was kept in a water bath at a constant temperature of 40° C. The sol was kept there for 20–24.5 hours depending on the used sol recipe. A certain amount of ethanol (445–480 mL) was evaporated to accelerate the reaction kinetics of the sol. The preparation of FIB 3 differed from the other sols with respect to the catalyst ($NH_3$ was used as catalyst in addition to $HNO_3$). $NH_3$ was added into the sol after 24 hours of aging at 40° C. The sol was vigorously stirred for 2 minutes. After stirring, the evaporation of ethanol was started.

After evaporation of ethanol the sols were cooled to either 20° C. or 0° C. (depending on the sample as shown in Table II). The spinning was started when a certain level of viscosity of the sol was reached. A rotational viscometer with a disc shaped spindle (Brookfield LVDV II+) was used to define the point where the spinning was started. The measurements were made at a constant shear rate of 3 rpm. To avoid breaking of the sol-gel filaments air bubbles were removed from the spinning solution under partial vacuum.

Dry spinning was used to prepare sol-gel fibers. The spinning solution was kept in a container whose temperature was adjustable. To push the spinning solution to a gear pump nitrogen gas was used. The gear pump (Zenith 958736) with a capacity of 0.6 mL/revolution metered the spinning solution to the spinning head. The spinneret was made of a gold/platinum mixture. The diameter of the holes was 65 μm and the l/d ratio was 1. The number of the holes was 6. The distance between the spinneret and the wind-up roll was adjusted to meet the demands of each fiber. After spinning, the fibers were dried in an oven at 50° C. for 2 hours. The drying can also be carried out at a lower temperature, or the drying step can be left out.

Aging

The ready-made fibers were aged in a desiccator at room temperature (−25° C.) for 2 weeks or 3 or 5 months.

Heat Treating

The fibers were placed in an oven and the temperature was raised at 10° C./hour to the top temperature (175° C. or 250° C.), where it was kept for 2 hours. Thereafter the temperature was allowed to drop to room temperature.

SBF Tests

The in vitro bioactivity tests were performed using a simulated body fluid (SBF)[31] that was prepared by dissolving reagent chemicals of NaCl, $NaHCO_3$, KCl, $K_2HPO_4 \cdot 3H_2O$, $MgCl_2 \cdot 6H_2O$, $CaCl_2 \cdot 2H_2O$ and $Na_2SO_4$ into deionised water. The fluid was buffered at physiological pH 7.40 at 37° C. with tris(hydroxymethyl)aminomethane and hydrocloric acid.

Three samples from each fiber batch at different aging times (shown in Table II) were used to investigate the reactions of the fibers in, SBF. Each specimen (10 mg) was immersed in 50 mL of SBF in a closed polyethylene container. Three samples of SBF enclosed in bottles without a specimen were used as controls to examine the solution stability. The samples were immersed in the SBF fluid for 2 weeks, the bottles being placed in a shaking water bath (Heto SBD 50 (shake 2, 36 mm, speed=160)) having a constant temperature at 37° C.

Ion Concentration Analysis

The calcium required for the HCA formation on the $SiO_2$ fiber surfaces were extracted from SBF. This was indicated by the reduction of the concentration of calcium in SBF. Sample solutions were monitored for calcium and silicon concentrations as a function of the immersion time. The calcium concentrations were determined with an atomic absorption spectrophotometer (AAS, Perkin-Elmer 460). The silicon concentrations were analysed by a molybdenum blue-method[33] with UV-Vis spectrophotometer (Hitachi Model 100-60). The silicon analysis was based on reduction with 1-amino-2-naphthol-4-sulfonic acid. All sample solutions were tested three times each.

Results

Effects of Aging

Figure 1D:
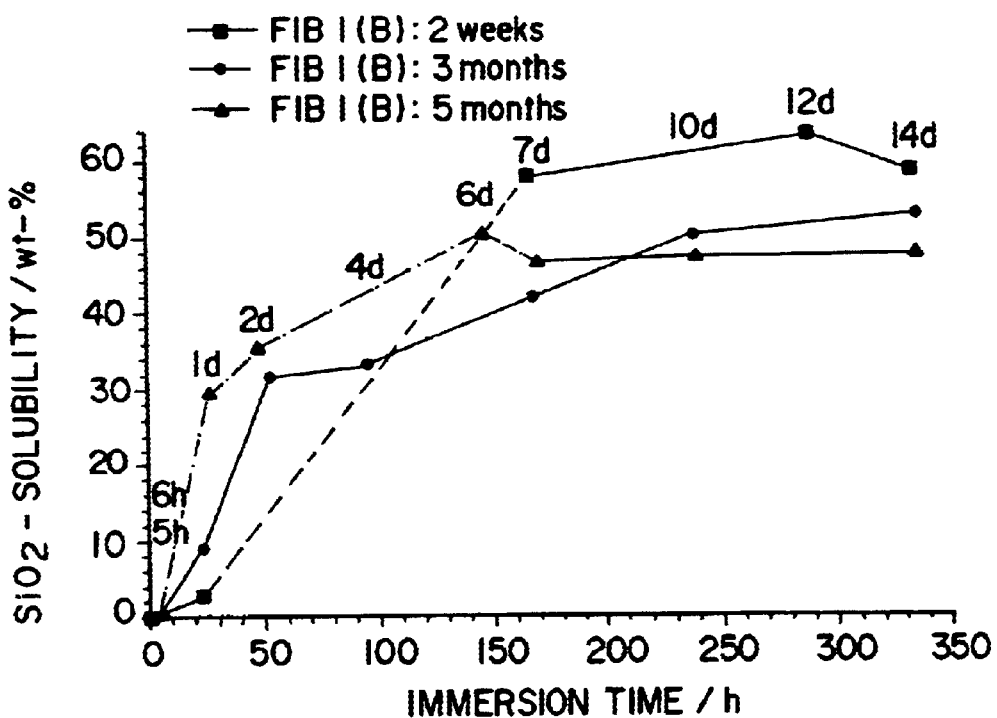
Figure 1E:
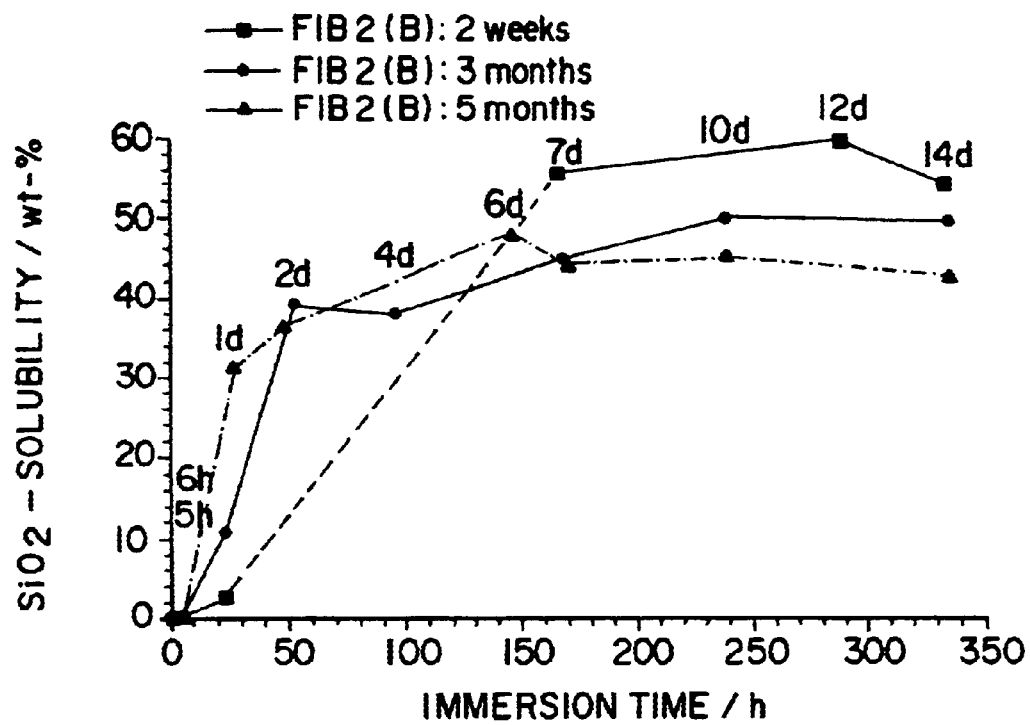
Figure 1F:
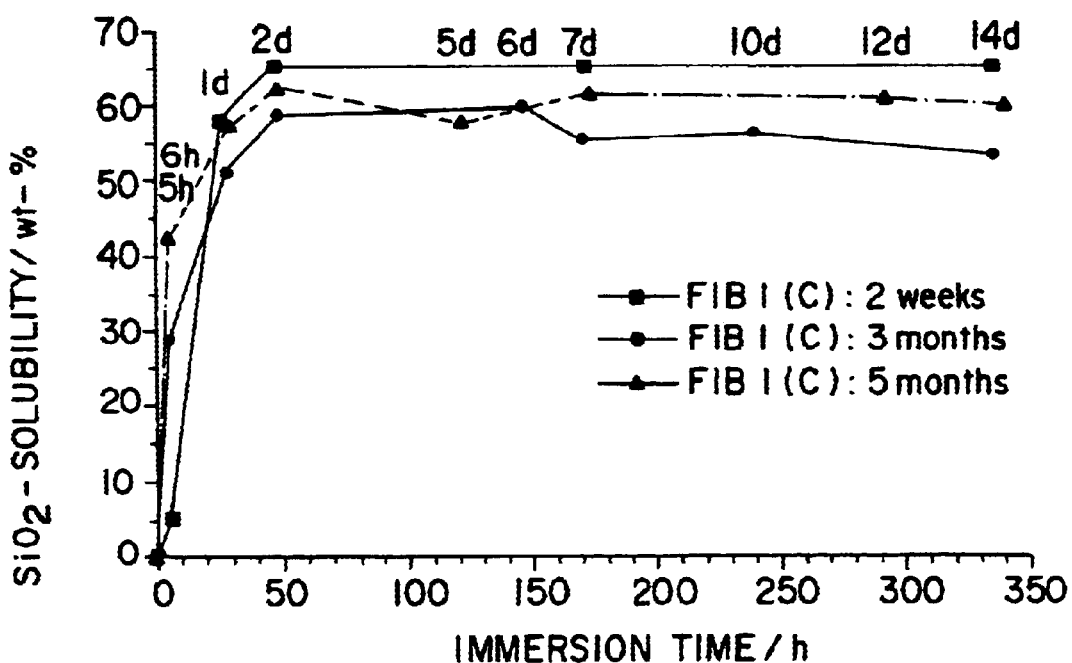
Figure 2A:
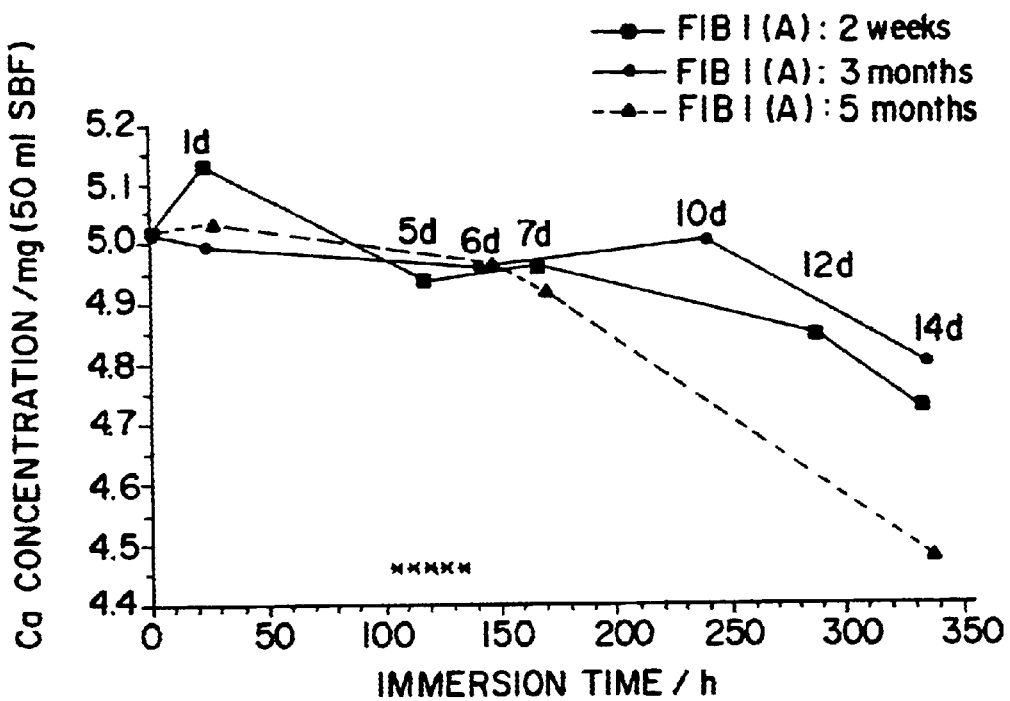
FIGS. 2a to 2f show the in vitro bioactivity (measured as the change of Ca concentration in the SBF solution) as function of immersion time in SBF for different sol-gel derived $SiO_2$ fibers aged for 2 weeks, 3 months and 5 months, respectively.
Figure 2B:
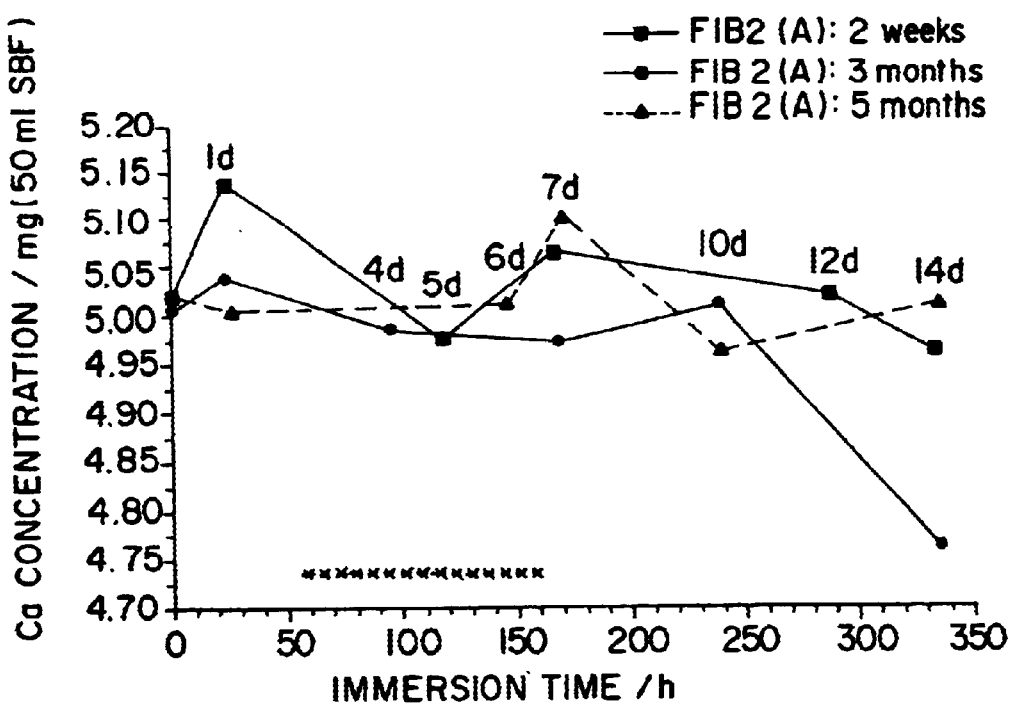
Figure 2C:
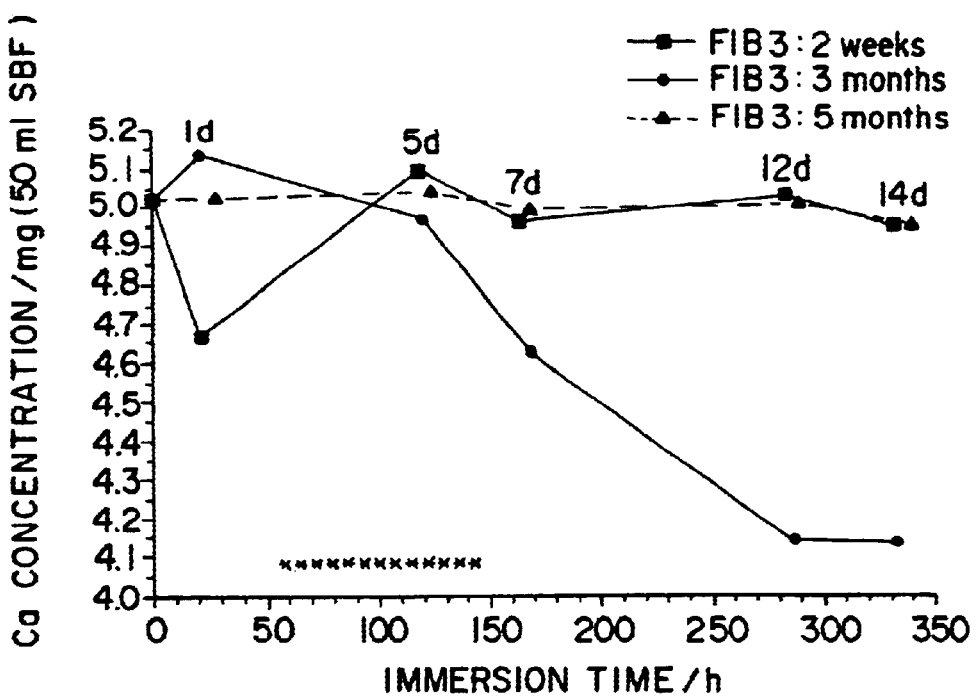
Figure 2D:
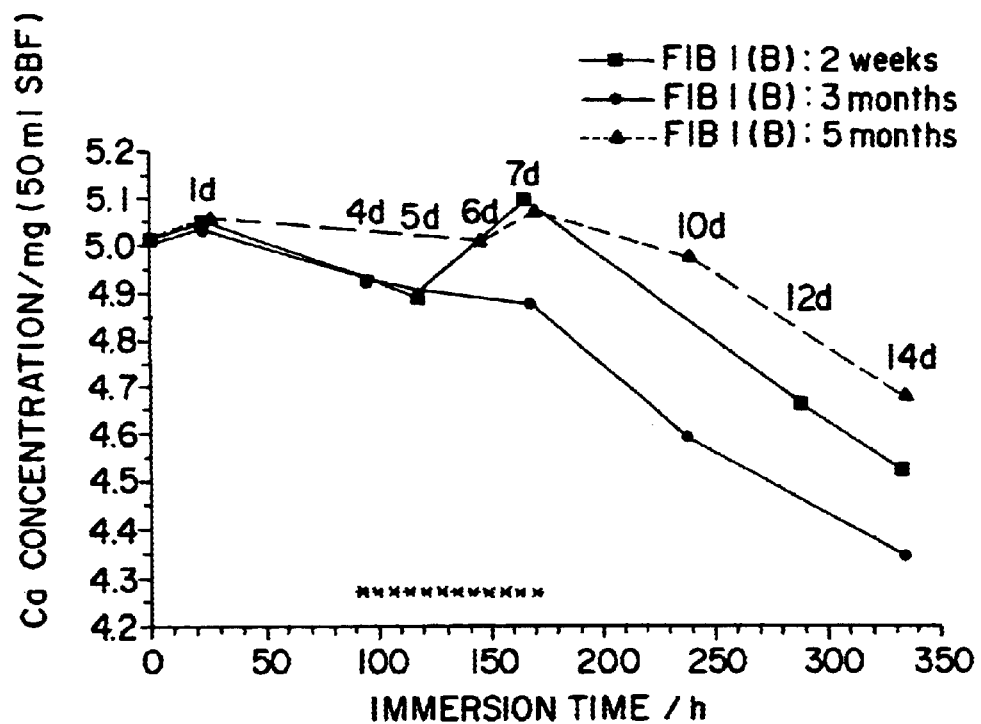
Figure 2E:
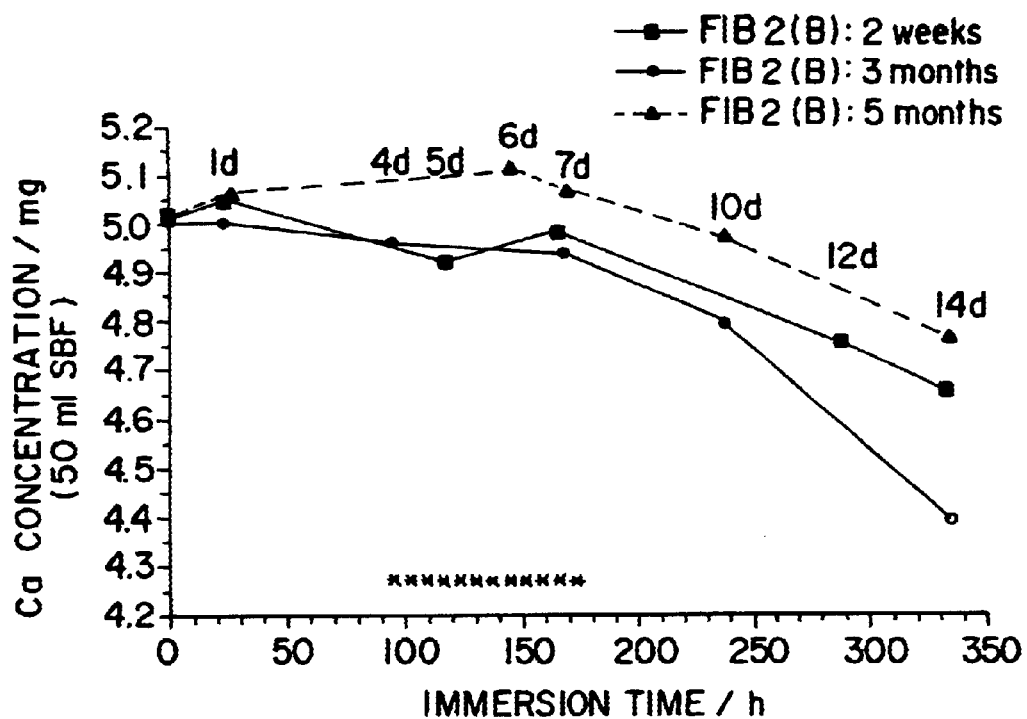
Figure 2F:
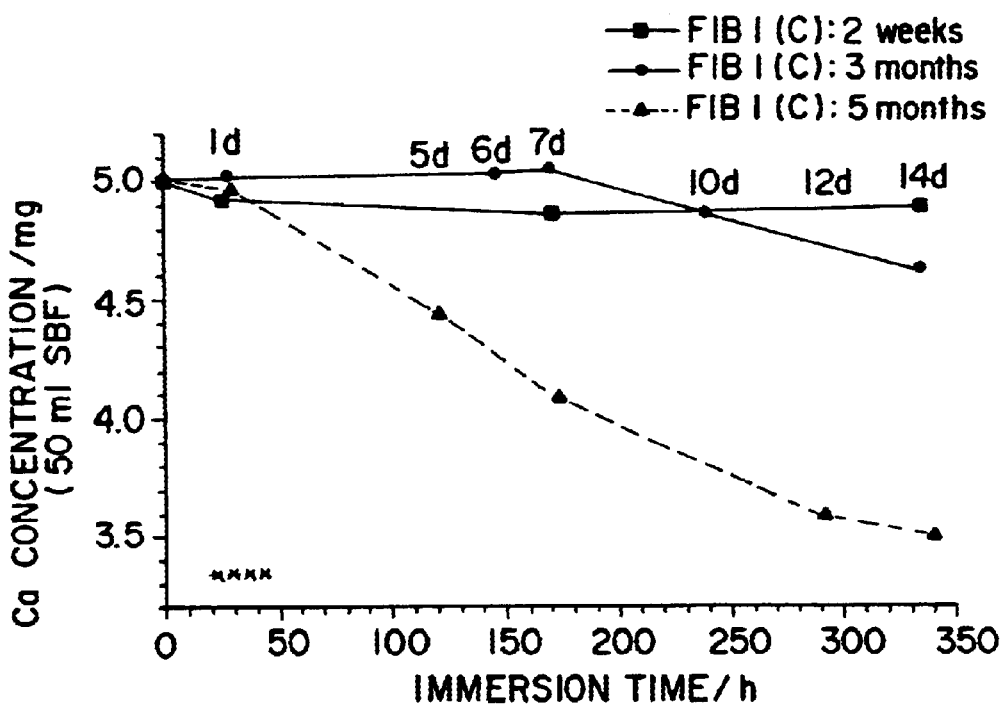

The solubility results of the fibers aged for 2 weeks, 3 and 5 months are shown in FIGS. 1a to 1f and summarised in Table II. Comparing the solubility results of the different fibers aged for 2 weeks, the solubility rates (before the saturation level) and saturation levels clearly differ from each other. The fibers spun in the later stage of spinnability (higher viscosity; FIB 1 (B) and FIB 2 (B)) were about ten times more soluble than the fibers having same sol compositions (Table I) but spun in the early stage of spinnability (FIB 1 (A) and FIB 2 (A)). The most soluble fiber (FIB 1 (C)) was spun in the later stage of spinnability. However, in this case the medium fiber diameter is smaller than for the others (shown in Table I), which may have a slight influence on the solubility. FIB 1 (C) had the same sol composition as FIB 1 (B), but the viscosity of the sol (FIB 1 (C)) was increased to 15000 cP before spinning. The solubility (saturation level) of the FIB 3 seemed to be a little bit lower than for the other fibers spun in the later stage of spinnability. As it is seen in FIGS. 1d to 1f, the solubility rates of FIB 1 (B), FIB 2 (B) and FIB 1 (C) are initially quite slow but start to increase faster before the saturation level is reached. This suggests that the outer structure of the fibers is denser than the inner structure. This property is also seen in other fibers, but not so clearly, suggesting more similar structure between the inner and outer structure. The differences between the solubility of the inner and outer structure have a clear influence on the given solubility rates (Table II) calculated from the linear portion of the curves before the saturation level. Therefore, the saturation level is also important for reliable comparison of the solubility rates of different fibers.

The stuctural stability of the fibers was investigated as a function of the aging time. For the FIB 1 (A) the solubility values were practically the same after 2 weeks, 3 and 5 months aging indicating a quite stable structure. The solubility rates of FIB 2 (A) aged for 3 or 5 months were higher than the solubility rate of FIB 2 (A) aged for 2 weeks. It suggests that the fibers become more fragile as a function of the aging time. However, the solubility rate of FIB 3 aged for 5 months was lower than the solubility rates of FIB 3 aged for 2 weeks or 3 months. This suggests a some degree of densification as a function of the aging time. As it is seen in the FIG. 1 (1d to 1f), the solubility rates of the outer structure of FIB 1 (B), FIB 2 (B) and FIB 1 (C) increase as a function of the aging time. However, the silica saturation levels seem to decrease as a function of the aging time. The solubilities of the fibers spun in the early stage of spinnability (FIB 1 (A) and FIB 2 (A)) differs from each other. However, the solubility rates and curves were nearly identical for the fibers having the same sol compositions but spun in the later stage of spinnability (FIB 1 (B) and FIB 2 (B)).

In FIGS. 2a to 2f, the in vitro bioactivity is illustrated as a decrease of the calcium concentration in the SBF as a function of the time. The bioactivity results are summarised in Table II. There was no direct connection between the in vitro bioactivity and $SiO_2$ solubility results (the silica concentration levels and saturation level). According to the silica solubility results the structure of the fibers seemed to change as a function of the aging time and so did the in vitro bioactivity.

In FIG. 2 the immersion time ranges where the silica saturation is reached are shown (indicated by asterisks). It is clearly seen that the calcium phosphate formation starts after the silica saturation point has been reached. According to the solubility results, the silica saturation level is achieved before 7 days of immersion in the SBF for every sample. However, some fibers did not form any calcium phosphate within the 2 weeks of immersion.

Effects of Heat Treatment

Figure 3A:
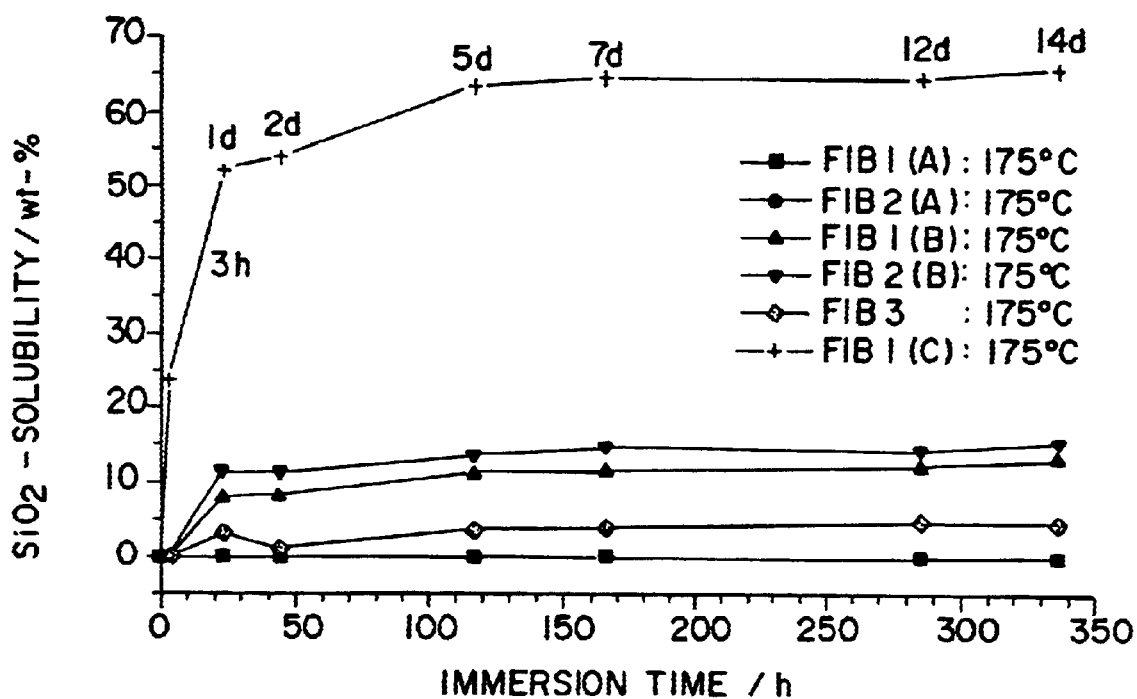
FIGS. 3a to 3c show the $SiO_2$ solubility as function of immersion time in SBF for different sol-gel derived $SiO_2$ fibers heat treated at 175° C. (a) or 250° C. (b), respectively.
Figure 3B:
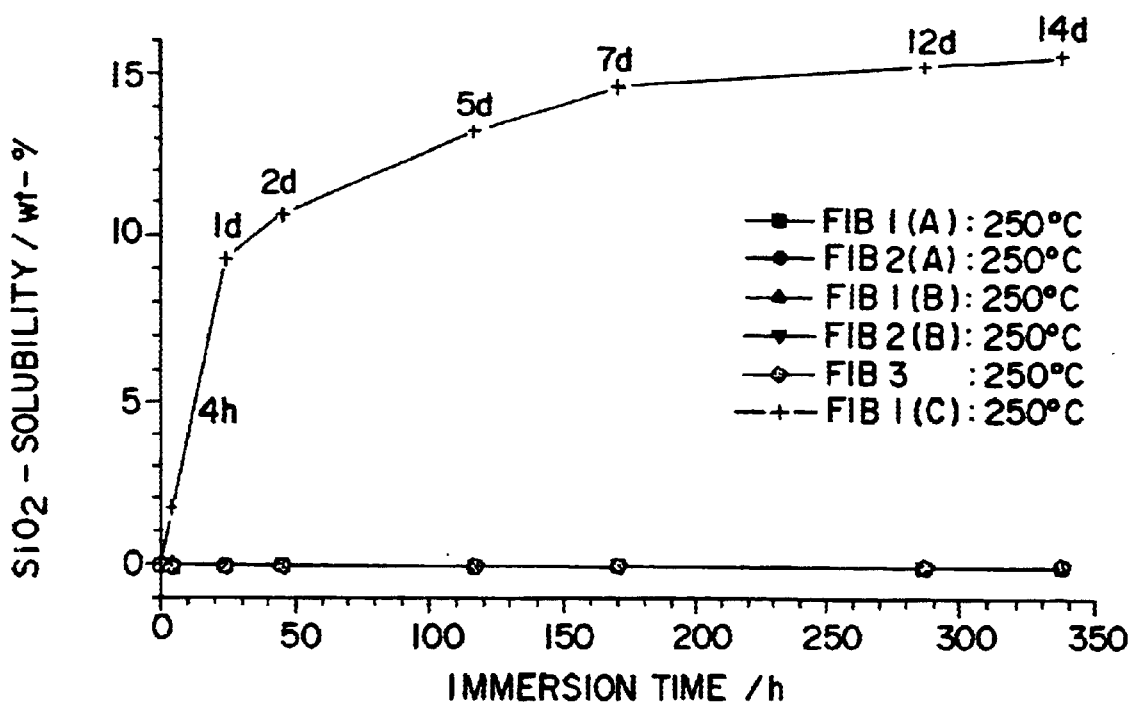
Figure 3C:
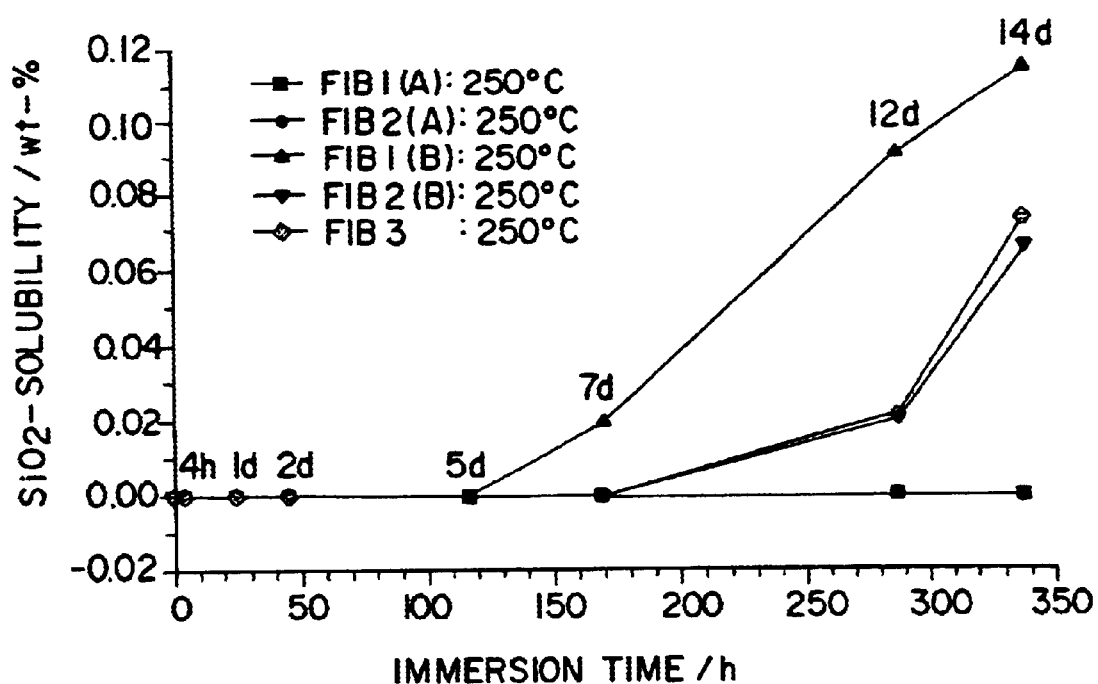
Figure 4A:
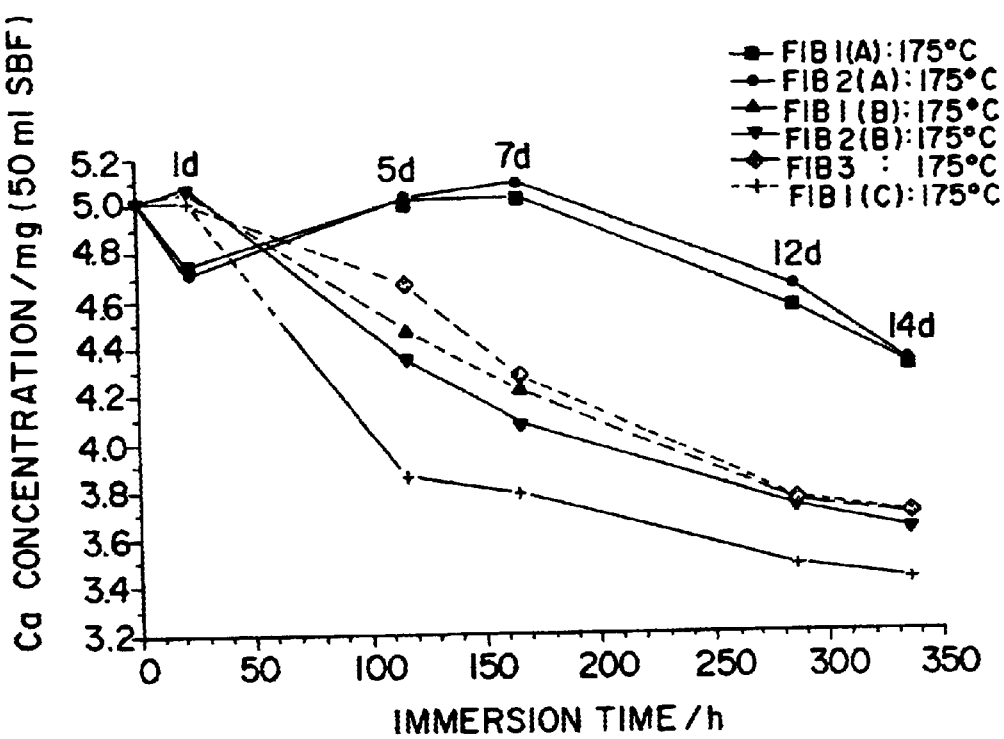
FIGS. 4a and 4b show the in vitro bioactivity (measured as the change of Ca concentration in the SBF solution) as function of immersion time in SBF for different sol-gel derived $SiO_2$ fibers heat treated at 175° C. (a) or 250° C. (b), respectively.
Figure 4B:
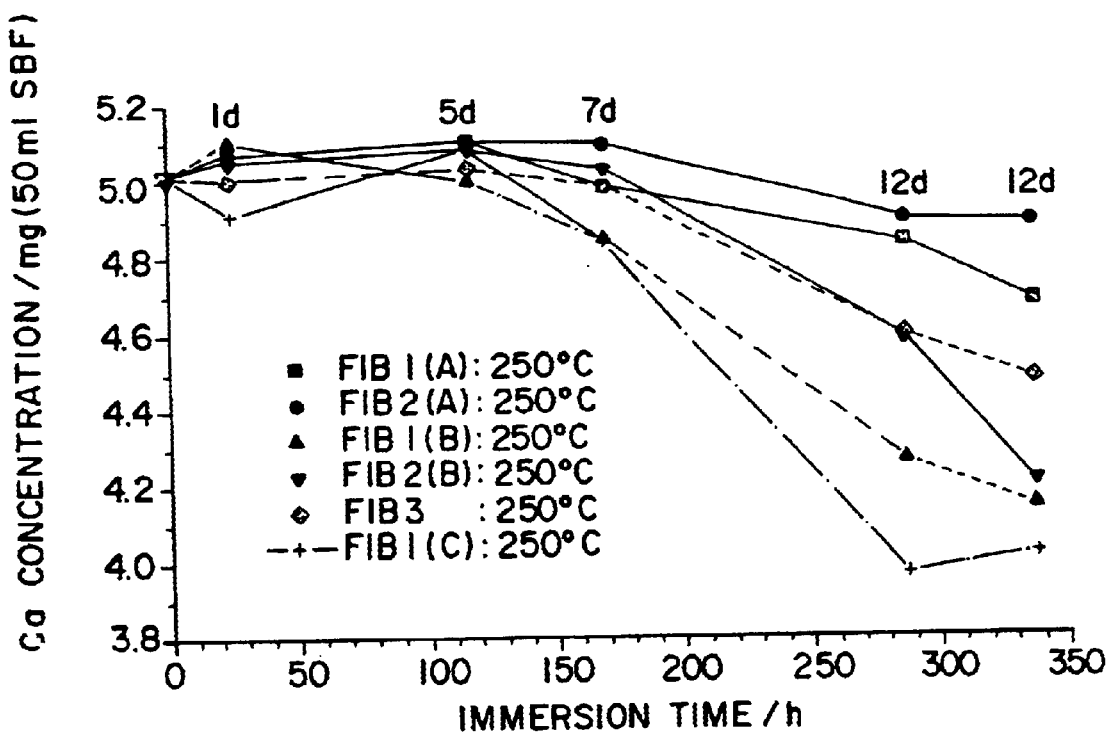

The results are shown in Table III and in the FIGS. 3a to 3b (solubility) and FIGS. 4a to 4b (in vitro bioactivity) for the two temperatures tested, 175 and 250° C., respectively.

When treated in 175° C., the solubility of all the fibers except for FIB 1 (C) decreased essentially, obviously because the structure became more dense. The speed of the HCA formation increased. When treated in 250° C., the solubility as well as the bioactivity decreased compared to that of the fibers treated in 175° C.

CONCLUSIONS

Figure 6:
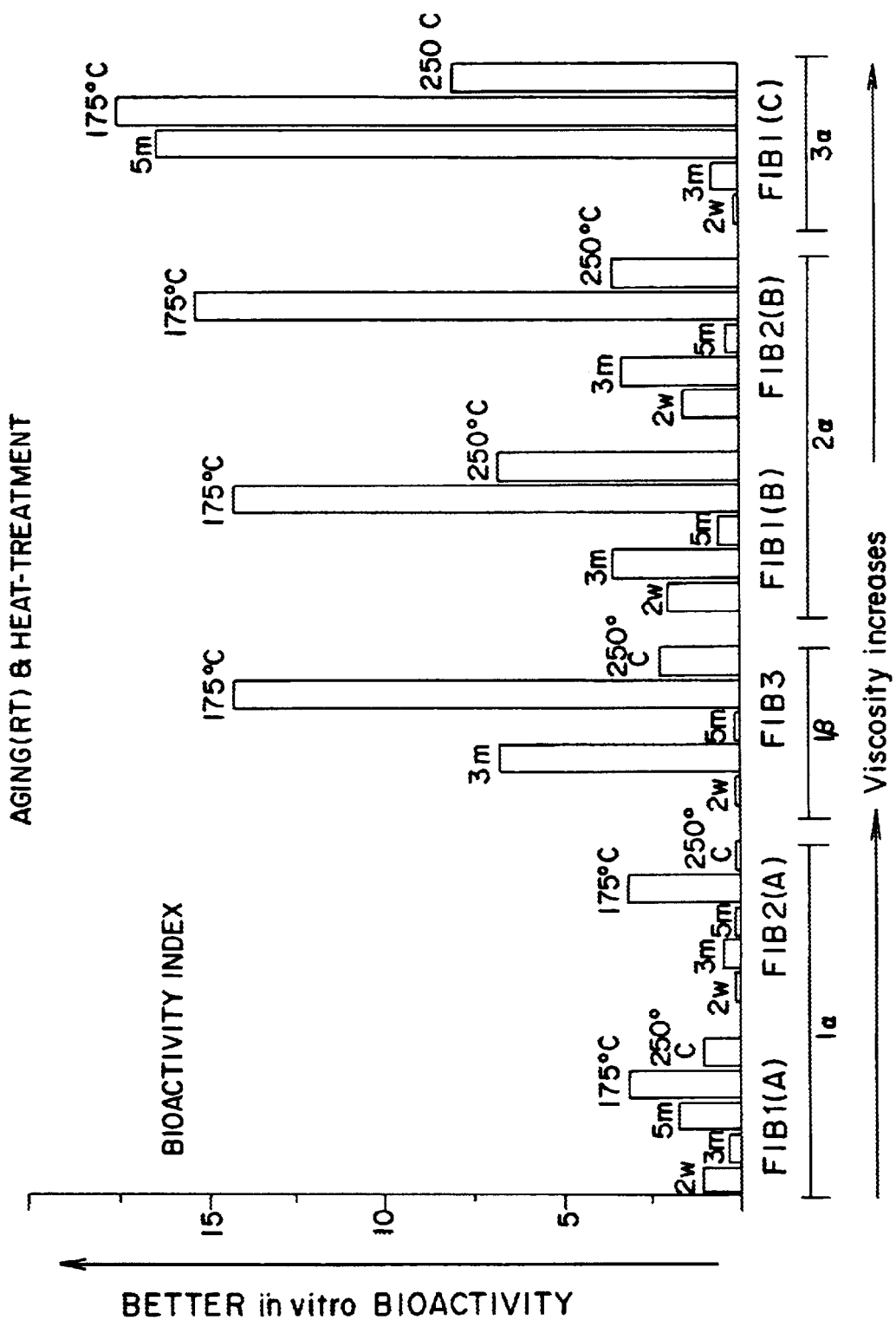
FIG. 6 shows the bioactivity index as function of sol viscosity at the start of fiber spinning, for sol-gel derived $SiO_2$ fibers aged for 2 weeks, 3 months or 5 months, or heat treated at 175° C. or 250° C.
Figure 7:
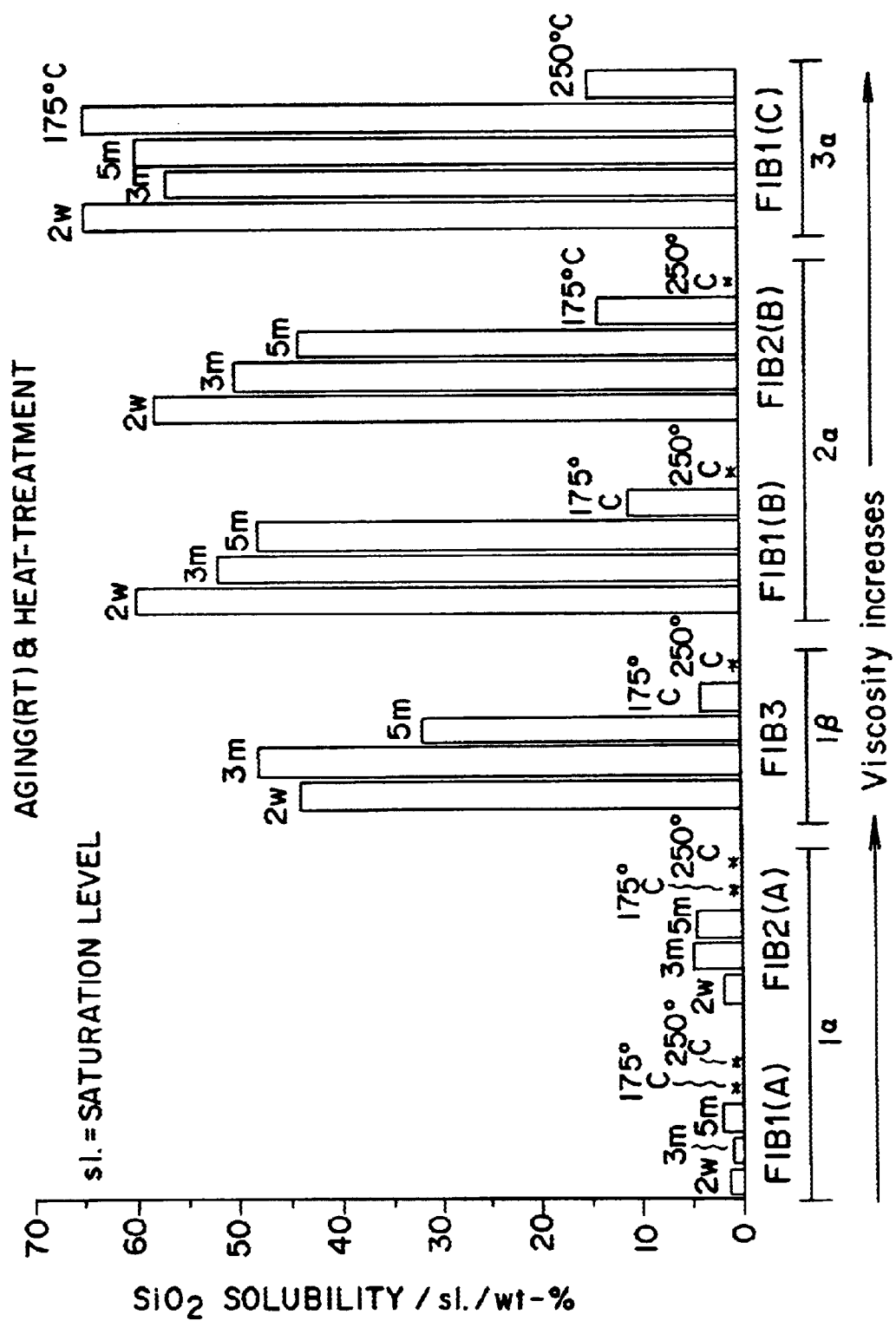
FIG. 7 shows the $SiO_2$ solubility measured as saturation level of silica in SBF as function of sol viscosity at the start of fiber spinning, for sol-gel derived $SiO_2$ fibers aged for 2 weeks, 3 months or 5 months, or heat treated at 175° C. or 250° C.
Figure 8:
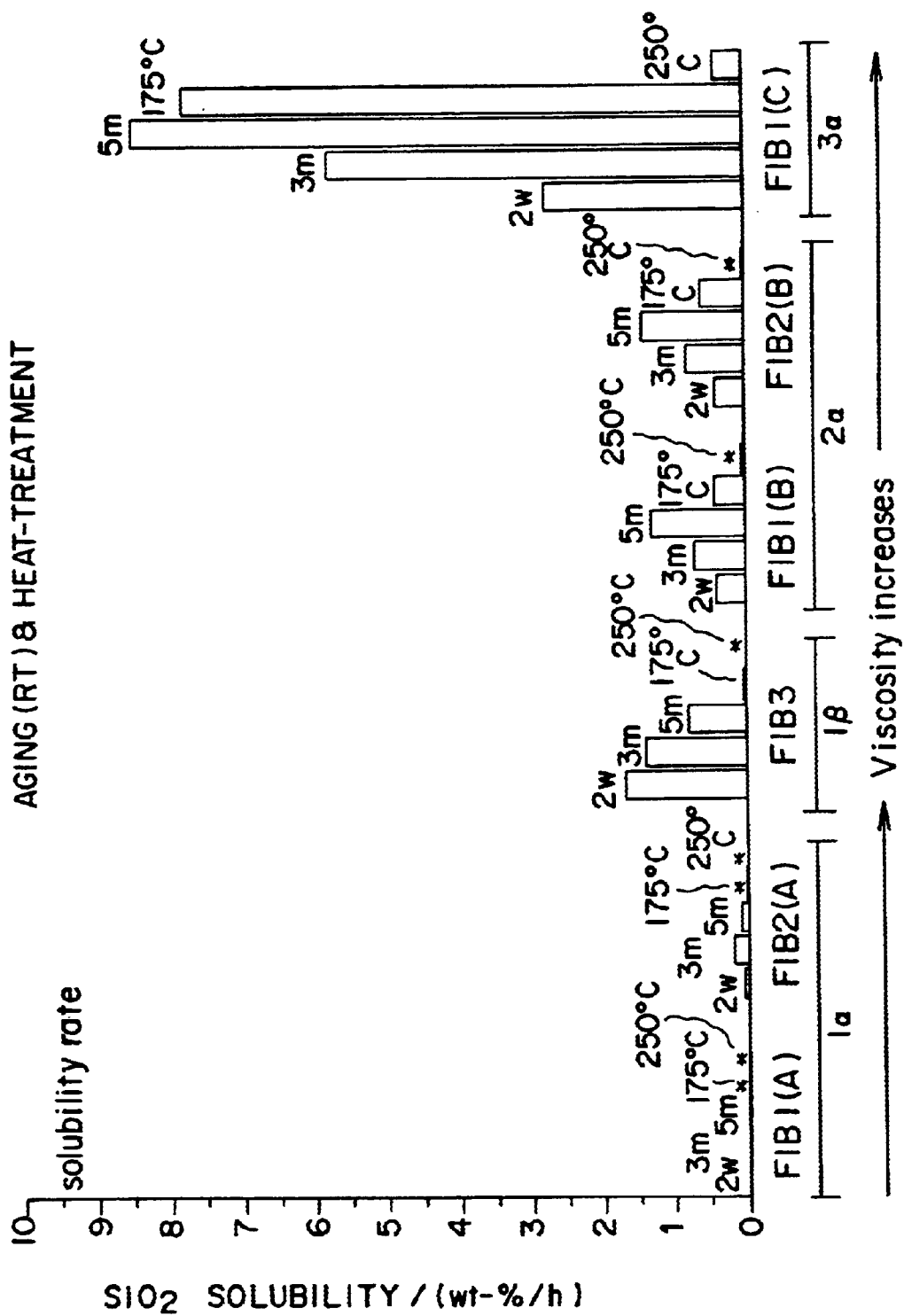
FIG. 8 shows the $SiO_2$ solubility in weight-% per hour (calculated from the linear portion of the curves before the silica saturation level) in SBF as function of sol viscosity at the start of fiber spinning, for sol-gel derived $SiO_2$ fibers aged for 2 weeks, 3 months or 5 months, or heat treated at 175° C. or 250° C.

FIGS. 6 to 8 summarize the effect of the different parameters on the bioactivity and solubility of the fibers prepared. The "bioactivity index" presented in FIG. 6 refers to the in vitro bioactivity studies and can be defined as a function of a) the starting point of the descent of the Ca concentration curve and b) the difference between the initial Ca concentration and the Ca concentration after 14 days. The calculation of the bioactivity index is best illustrated by referring to the following example: From FIG. 2c it can be seen that the start of the descent of the Ca concentration curve for FIB 3, 3 months, takes place after 5 to 7 days (6 days, as an average) time of immersion. The end point (14 days) minus the starting point (6 days) is 8. The difference between the starting Ca concentration (5.0 mg/50 ml) and the end point Ca concentration (4.15 mg/50 ml) is 0.85. The bioactivity index is the product 8×0.85=6.8.

Factors Determining Bioactivity

The structure of the fiber matrix is the most important factor controlling the in vitro bioactivity of the silica fibers. The structure of the fibers can be varied using three different factors: (1) use of the spinnable sols having varying structure and size of silica polymers establishing varying viscosity levels, (2) aging of the green state fibers and (3) heat-treatment of fibers.

Figure 5:
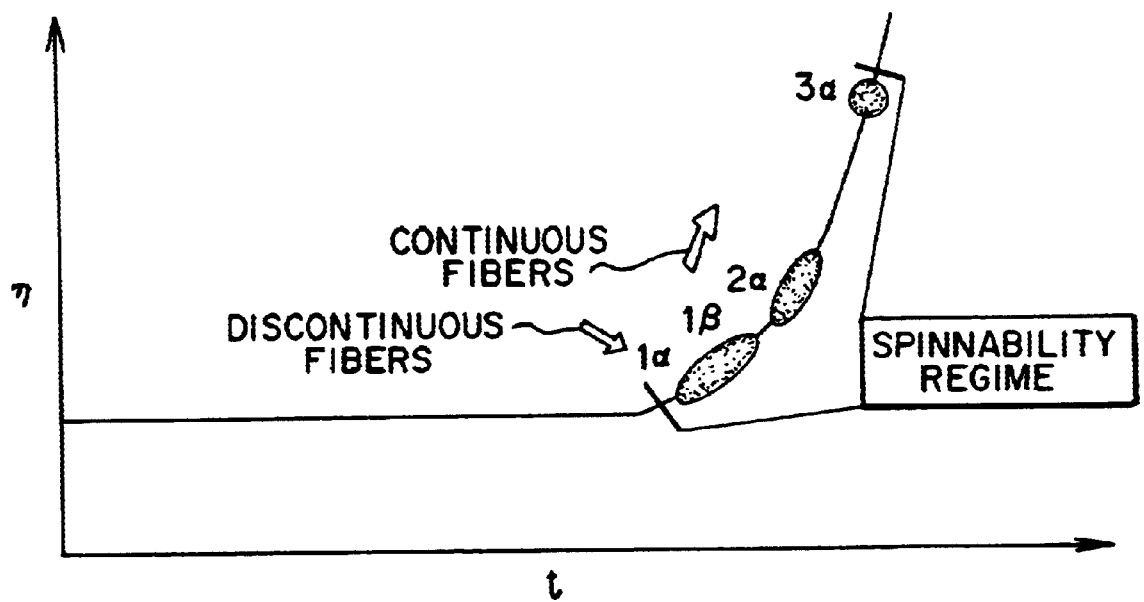
FIG. 5 shows the viscosity of the spinning sol versus time and indicates the spinnability regime for spinning the different sol-gel derived $SiO_2$ fibers.

The spinnable sol can roughly be divided into three different regimes: $\eta<3000$ cP ($1\alpha$ & $1\beta$), $\eta=3000$–$5000$ cP ($2\alpha$) and $\eta=15\,000$ cP ($3\alpha$). They are illustrated in FIG. 5. FIB1(A), FIB2(A) and FIB3 belong to the same group according to the viscosity level, but FIB1(A) and FIB2(A) are marked as $1\alpha$, because they have been spun at $0°$ C., which causes increase in the viscosity.

A general trend of the varying bioactivity is shown in FIG. 6. The higher the starting viscosity is in the spinning sol, the better is the bioactivity. In addition, the solubility data of the fibers (shown in FIGS. 7 and 8) follow the same pattern. The solubility rate of silica as well as the saturation point concentration are greater as the bioactivity increases.

Another clearly observable property is the influence of the heat-treatment. As compared to the green state fibers (dried at $50°$ C. & aged at RT), increased bioactivity is achieved for every sample as they are heat-treated at $175°$ C. and it declines after the heat-treatment at $250°$ C.

The aging of the fibers had no common behaviour with respect to the in vitro bioactivity. The fibers spun at lower viscosities ($1\alpha$) only show that the bioactivity is not very good and the differences are not great. For the fibers spun at higher viscosities ($1\beta$ & $2\alpha$), the bioactivity shows best results after 3 months of aging. In addition, the properties of these fibers seem to vary according to same pattern as they are aged and heat-treated. The fiber (FIB 1 (C)) spun at the highest viscosity ($3\alpha$) becomes better with aging (up to 5 months).

As a summary, it can be said that the fibers spun at $\eta>3000$ cP have good properties with respect to the bioactivity and a more porous structure which is observed in the solubility data. The fibers spun at $\eta<3000$ cP have a condensed structure and they are structurally more stable (less soluble in the simulated body fluid (SBF)) and the bioactivity is clearly lower. Heat-treatment at $175°$ C. was favourable for every sample.

Factors Determinining the Structure of the Fibers

Within the same recipe and also the viscosity groups, there are differences depending on the small structural changes. All the factors which have already been mentioned have an influence on the fiber structure (size and form of the silica polymers in the sol, the viscosity of the sol, aging time and heat-treatment).

The size and form of the silica polymers is an important factor influencing the fiber structure and these properties also are interconnected with the viscosity of the sol. At lower viscosities, the silica polymers are smaller and they are packed easier (producing more condensed structures) than larger polymer at higher viscosities. Also the viscosity level as such has an influence on the structure, Higher viscosity may retard the orientation of the silica polymers in spinning leaving the resulting structure more porous. These factors determine the connection between the viscosity (and the size and form of the silica polymers): the higher the viscosity (the larger the polymer size), the higher solubility (more porous structure).

The influence of the heat-treatment at 175 or $250°$ C. is obvious. A morphologically suitable surface for HCA formation is produced at $175°$ C. The heat treatment consolidates the fiber matrix and makes the structure less soluble in SBF. However, FIB 1 (C) which was spun at high viscosity seem to obtain the same favourable properties with 5 months' aging. This fiber has the highest solubility of all and hence also the most porous structure. However, the silica saturation levels are so high that it is difficult to use them reliably in comparisons. On the other hand, the solubility rates provide information from the fiber surface and the analogy for the aging and heat-treatment is same as for the other samples. Although the structure is porous, it also has the longest polymers and the fiber structure is most favourable, In other words, the silica polymers are best to resist the structural changes (e.g. caused by mild heat-treatment at $175°$ C.) although they form a more porous structure.

The changes observed within the same viscosity groups or in aging for a particular recipe have various explanations. The structures of the sols and fibers belonging to the first group, $1\,\alpha$ (FIB 1(A) and FIB2(A)) are slightly different. The solubility data (FIGS. 7 and 8) shows (indirectly) that FIB2(A) is more porous than FIB 1(A). Also transmission electron micrographs verify this fact. The sol composition is already slightly different, FIB2(A) contains more catalysts (nitric acid) than FIB 1(A). The reactions proceed a bit faster for FIB2(A), which produces more branched polymers and hence more porous structure. Also during aging there are differences due to catalyst concentration and still proceeding reactions.

The fibers belonging to the group $2\alpha$ (FIB 1(B) ja FIB2(B)) have almost identical properties as a function of aging and heat-treatment. These fibers provide a good example on the influence of the spinning moment on the fiber structure. They are from the recipe as the FIB 1(A) and FIB2(A), but they have been spun later at higher viscosity.

FIB3 has intermediate properties, which are, on the other hand, quite similar to those of FIB1(B) and FIB2(B). FIB3 has also a viscosity value near the regime $2\alpha$, although lower. However, it is the only fiber sol containing $NH_3$, which catalyses the condensation reactions and the viscosity increases faster than for the other samples.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

TABLE I

Sol Compositions in Molar Ratios and Cross-Sectional Diameters of the Fibers

| Symbol of the Fiber Samples | r = $H_2O$/ TEOS | EtOH/ TEOS | $HNO_3$/ TEOS | $NH_3$/ TEOS | Diameters of the fibers[a] min.-max. ($\mu$m) | Diameters of the fibers[a] Medium Value ($\mu$m) |
|---|---|---|---|---|---|---|
| FIB 1 (A) | 2 | 1 | 0.036 | 0 | 39–79 | 59 |
| FIB 2 (A) | 2 | 1 | 0.1 | 0 | 30–82 | 53 |
| FIB 3 | 2 | 1 | 0.1 | 0.01 | 21–68 | 39 |
| FIB 1 (B) | 2 | 1 | 0.036 | 0 | 34–60 | 48 |
| FIB 2 (B) | 2 | 1 | 0.1 | 0 | 26–67 | 52 |
| FIB 1 (C) | 2 | 1 | 0.036 | 0 | 14–50 | 23 |

[a]The diameters of the fibers were measured before first immersion in SBF. 50 samples were taken from each fiber batch to measure the average diameters.

TABLE II

In vitro solubility and bioactivity for aged fibers

| Symbol of the Fiber Samples | $SiO_2$ (fiber matrix) solubility 2 weeks wt-%/h[a] | 2 weeks sl.[b]/wt-% | 3 months wt-%/h[a] | 3 months sl.[b]/wt-% | 5 months wt-%/h[a] | 5 months sl.[b]/wt-% | Calcium Phosphate Formation Begins 2 weeks /d | 3 months /d | 5 months /d | Viscosity /Pas |
|---|---|---|---|---|---|---|---|---|---|---|
| FIB 1 (A) | 0.02 | 1.5 | 0.03 | 1.2[c] | 0.03 | 2.0[c] | 12–14 | 10–14 | 7–14 | 2.0[d] |
| FIB 2 (A) | 0.03 | 2.0 | 0.2 | 5.0 | 0.1 | 4.6 | —[f] | 10–14 | —[f] | 2.0[d] |
| FIB 3 | 1.7 | 44 | 1.4 | 48 | 0.8 | 32 | —[f] | 5–7 | —[f] | 2.0[e] |
| FIB 1 (B) | 0.4[g] | 60 | 0.7 | 52 | 1.3 | 48 | 7–12 | 7–10 | 10–14 | 3.9[e] |
| FIB 2 (B) | 0.4[g] | 58 | 0.8 | 50 | 1.4 | 44 | 7–12 | 7–10 | 10–14 | 3.0[e] |
| FIB 1 (C) | 2.8 | 65 | 5.8 | 57 | 8.5 | 60 | —[f] | 10–14 | 1–5 | 15[d] |

[a]Calculated from the linear portion of the curves before the saturation level between 0 to 2 days of immersion.
[b]sl. = The saturation level of the silica solubility in 50 mL SBF.
[c]Clear saturation level was not detected. The given value is the silica solubility level after 2 weeks of immersion in SBF.
[d]The viscosity of the sol before spinning the fibers at 0° C. or [e]20° C.
[f]Fibers did not form any calcium phosphate within the 2 weeks of immersion in SBF.
[g]The point at 2 days is missing due to technical problems lowering slightly the real solubility value.

TABLE III

In vitro solubility and bioactivity for heat treated fibers

| Symbol of the Fibre Samples | $SiO_2$ (fiber matrix) solubility 175° C. (wt-%/h)[a] | 175° C. sl.[b]/(wt-%) | 250° C. (wt-%/h)[a] | 250° C. sl.[b]/(wt-%) | Calcium Phosphate Formation Begins 175° C. /d | 250° C. /d |
|---|---|---|---|---|---|---|
| FIB 1 (A) | 0.0 | 0.0 | 0.0 | 0.0 | 7–12 | 7–14 |
| FIB 2 (A) | 0.0 | 0.0 | 0.0 | 0.0 | 7–12 | —[d] |
| FIB 3 | 0.03 | 4.0 | 0.0004 | —[c] | 1–5 | 7–12 |
| FIB 1 (B) | 0.4 | 11 | 0.0005 | —[c] | 1–5 | 5–7 |
| FIB 2 (B) | 0.6 | 14 | 0.0004 | —[c] | 1–5 | 7–12 |
| FIB 1 (C) | 7.8 | 65 | 0.4 | 15 | 1–5 | 5–7 |

[a]Calculated from the linear portion of the curves before the silica saturation level.
[b]sl. = The saturation level of the silica solubility in 50 mL SBF.
[c]Clear saturation level was not detected within the 2 weeks of immersion in SBF.
[d]Fibers did not form any calcium phosphate within the 2 weeks of immersion in SBF.

REFERENCES

1. Hashimoto T, Kamiya K, Nasu H. Strengthening of sol-gel-derived $SiO_2$ glass fibers by incorporating colloidal silica particles. J. Non-Cryst Sol 1992;143:31–39.
2. Pozo de Fernandez M E, Kang C, Mangonon P L. Process ceramic fibers by sol-gel. Chem Eng Prog 1993;9:49–53.
3. Sakka S, Kamiya K. The sol-gel transition in the hydrolysis of metal alkoxides in relation to the formation of glass fibers and films. J Non-Cryst Sol 1982;48:31–46.
4. Sakka S, Kozuka H. Rheology of sols and fiber drawing. J Non-Cryst Sol 1988;100:142–153.
5. Shin D-Y, Han S-M. Spinnability and Theological properties of sols derived from $Si(OC_2H_5)_4$ and $Zr(O-nC_3H_7)_4$ solutions. J Sol-Gel Sci Tech 1994;1:267–273.
6. Sowman H G. A new era in ceramic fibers via sol-gel technology. Cer Bull 1988;67:1911–1916.
7. Sacks M D, Sheu R-S. Rheological properties of silica sol-gel materials. J Non-Cryst Sol 1987;92:383–396.
8. Hasegawa I, Nakamura T, Motojima S, Kajiwara M. Synthesis of silicon carbide fibers by sol-gel processing. J Non-Cryst Sol 1997;8:577–579.

9. Brinker C J, Scherer G W. Sol-Gel Science: The Physics and Chemistry of Sol-Gel Processing. Academic Press Inc. San Diego. Calif. USA; 1990. p 204–209.

10. Kamiya K, Tanimoto K, Toshinobu Y. Preparation of TiO2 fibers by hydrolysis and polycondensation of Ti(O-i-$C_3H_7$)$_4$. J Mat Sci Lett 1986;5:402–404.

11. Glaubitt W, Watzka W, Scholz H, Sporn D. Sol-gel processing of functional and structural ceramic oxide fibers. J Sol-Gel Sci Tech 1997;8:29–33.

12. Muralidharan B G, Agrawal D C. Sol-gel derived $TiO_2$—$SiO_2$ fibers. J Sol-Gel Sci Tech 1997;9:85–93.

13. Toyoda M, Hamaji Y, Tomono K. Fabrication of $PbTiO_3$ ceramic fibers by sol-gel processing. J Sol-Gel Sci Tech 1997;9:71–84.

14. Sakka S. Sol-gel processing of insulating, electroconducting and superconducting fibers. J Non-Cryst Sol 1990;121:417–423.

15. Del Olmo L, Caldaza M L. $PbTiO_3$ ceramic fibers prepared from a sol-gel process as piezoelectric materials. J Non-Cryst Sol 1990;121:424–427.

16. Yoko T, Kamiya K, Kanaka K. Preparation of multiple oxide $BaTiO_3$ fibers by the sol-gel method. J Mat Sci 1990;25:3922–3929.

17. Katayama S, Sekine M. Fabrication of superconducting $YBa_2Cu_3O_7$-x fibers by the sol-gel method using metal alkoxides. J Mater Res 1991;6:1629–1633.

18. Venkatasusubramanian N, Wade B, Desai P, Abhiraman. Synthesis and characterization of spinnable sol-gel derived polyborates. 3 Non-Cryst Sol 1991;130:144–156.

19. Selvaraj U, Prasadarao A V, Komaneni S, Brooks K, Kurtz S. Sol-Gel processing of $PbTiO_3$ and $Pb(Zr_{0.52}Ti_{0.48})$$O_3$ fibers. J Mat Res 1992;7:992–996.

20. Yogo T, Iwahara H. Synthesis of $\alpha$-alumina fiber from modified aluminium alkoxide precursor. J Mat Sci 1992;27:1499–1504.

21. Seddon A B. Applicability of sol-gel processing in production of silica based optical fibers. Mat Sci Tech 1993;9:729–736.

22. Emig G, Fitzer E, Zimmerman-Chopin R. Sol-gel process for spinning of continuous $(Zr,Ce)O_2$ fibers. Mat Sci Eng 1994;A189:311–317.

23. Emig G, Wirth R, Zimmermann-Chopin R. So/gel-based precursors for manufacturing refractory oxide fibers. J Mat Sci Lett 1994;29:4559–4566.

24. Chiou Y H, Tsai M T, Shih H C. The preparatin of alumina fiber by sol-gel processing. J Mat Sci 1994;29:2378–2388.

25. Narang U, Gvishi R, Bright F V, Prasad P N. Sol-gel-derived micron scale optical fibers for chemical sensing. J Sol-Gel Sci Tech 1996;6:113–119.

26. Hasegawa I, Nakamura T, Kajiwara M, Motojima S. Synthesis of silicon carbide fibers by sol-gel processing. J Sol-Gel Sci Tech 1997;8:577–579.

27. Matejec V, Hayer M, Pospíšilová M, Kasík I. Preparation of optical cores of silica optical fibers by the sol-gel method. J Sol-Gel Sci Tech 1997;8:889–893.

28. Jokinen M, Peltola T, Veittola S, Rahiala H, Rosenholn J B. Biodegradable ceramic fibres from silica sols. J Eur Ceram Soc (submitted).

29. Hench L. Bioactive ceramics: Theory and clinical applications. Bioceramics 1994;7:3–14.

30. Voigt C, Müller-Mai C, Kandilakis K, Kangasniemi I, Yli-Urpo A, Gross U. Biological reaction after implantation of sol-gel.activated titanium cylinders in the distal epiphysis of the rabbit femur. $13^{TH}$ European Conference on Biomaterials. Göteborg. Sweden; 1997. p 45.

31. Li P, Ohtsuki C, Kokubo T, Nakanishi K, Soga N, Kanamura T, Yamamuro T. Apatite formation induced by silica gel in a simulated body fluid. J Am Ceram Soc 1992;75:2094–97.

32. Kokubo T, Kushitani H, Sakka S, Kitsugi T, Yamamuro T. Solutions able to reproduce in vivo surface-structure changes in bioactive glass-ceramic A-W$^3$. J Biomed Mater Res 1990;24:721.

33. Koch O G, Koch-Dedic G A. Handbuch der Spurenanalyse. Berlin: Springer-Verlag; 1974. p 1105.

34. Rehman I, Bonfield W. Characterization of hydroxyapatite and carbonated apatite by photo acoustic FTIR spectroscopy. J Mater Science. Mater Medicine 1997;8:14.

35. Peltola T, Jokinen M, Rahiala H, Levänen E, Rosenholm J B, Kangasniemi I, Yli-Urpo A. Calcium phosphate formation on porous sol-gel-derived $SiO_2$ and $CaO$-$P_2O_5$—$SiO_2$ substrates in vitro. J Biomed Mater Res 1999, 44:12–21.

36. Pereira M M, Hench L L. Mechanisms of hydroxyapatite formation on porous gel-silica substrates. J Sol-Gel Sci Tech 1996;7:59–68.

37. Andersson Ö H, Kangasniemi I. Calcium phosphate formation at the surface of bioactive glass in vitro. J Biomed Mater Res 1991;25:1019–1030.

38. Peltola T, Jokinen M, Rahiala H, Pätsi M, Heikkilä J, Kangasniemi I, Yli-Urpo A. Effect of aging time of sol on structure and in vitro calcium phosphate formation of sol-gel derived titania films. J Biomed Mater Res (submitted).

39. Jokinen M, Pätsi M, Rahiala H, Peltola T, Ritala M, Rosenholm Jarl B. Influence of sol and surface properties on in vitro bioactivity of sol-gel derived $TiO_2$ and $TiO_2$—$SiO_2$ films deposited by dip coating method. J Biomed Mater Res 1998;42:295–302.

What is claimed is:

1. A method for the preparation of a bioactive silica fiber, said method comprising spinning a solution containing silica polymers to form a fiber, wherein the starting point of said spinning step corresponds to a solution viscosity of at least 2000 cP, followed by (i) heat treating or ii) aging of the fiber.

2. The method according to claim 1 wherein the viscosity is at least 3000 cP.

3. The method according to claim 1 wherein the fiber is heat treated for two hours or more at a temperature in the range of 150 to 250° C.

4. The method according to claim 3 wherein the temperature range is 150 to 200° C.

5. The method according to claim 2 wherein the fiber is heat treated for a sufficient period of time in a temperature in the range 150 to 250° C.

6. The method according to claim 5 wherein the temperature range is 150 to 200° C.

7. The method according to claim 2 wherein the fiber is aged for about 2 weeks to 5 months.

8. The method according to claim 7 wherein the fiber is aged for about 3 to 5 months.

9. The method according to claim 2 wherein the fiber is aged for about 2 weeks to 5 months.

10. The method according to claim 9 wherein the fiber is aged for about 3 to 5 months.

11. A bioactive silica fiber spun from a solution containing silica polymers at a starting point of a spinning process corresponding to a solution viscosity of at least 2000 cP, after which said fiber has been subjected to i) heat treatment or ii) aging.

12. The fiber according to claim 11 wherein said viscosity is at least 3000 cP.

13. The fiber according to claim 11 wherein said fiber has been heat treated for a sufficient period of time in a temperature in the range 150 to 250° C.

14. The fiber according to claim 13, said fiber having been heat treated in the temperature range 150 to 200° C.

15. The fiber according to claim 12 wherein said fiber has been heat treated for a sufficient period of time in a temperature in the range 150 to 250° C.

16. The fiber according to claim 15, said fiber having been heat treated in the temperature range 150 to 200° C.

17. The fiber according to claim 11 wherein said fiber has been aged for about 2 weeks to 5 months.

18. The fiber according to claim 17 wherein said fiber has been aged for about 3 to 5 months.

19. The fiber according to claim 12 wherein said fiber has been aged for about 2 weeks to 5 months.

20. The fiber according to claim 19 wherein said fiber is aged for about 3 to 5 months.

21. The fiber according to any of the claims 11 to 20 wherein said fiber also comprises a biologically active agent.

* * * * *

UNITED STATES PATENT AND TRADEMARK OFFICE
CERTIFICATE OF CORRECTION

PATENT NO. : 6,632,412 B2  Page 1 of 1
DATED : October 14, 2003
INVENTOR(S) : Timo Peltola et al.

It is certified that error appears in the above-identified patent and that said Letters Patent is hereby corrected as shown below:

Column 12,
Line 55, change "claim 2" to -- claim 1 --.

Column 14,
Line 9, change "any of the claims 11 to 20" to -- claim 11 --.

Signed and Sealed this

Fourteenth Day of December, 2004

JON W. DUDAS
*Director of the United States Patent and Trademark Office*